United States Patent
Chen et al.

(10) Patent No.: US 9,888,923 B2
(45) Date of Patent: Feb. 13, 2018

(54) FIRING ASSEMBLY FOR SURGICAL STAPLER AND SURGICAL STAPLER

(71) Applicant: Touchstone International Medical Science Co., Ltd., Jiangsu (CN)

(72) Inventors: Wangdong Chen, Jiangsu (CN); Wei Xu, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 413 days.

(21) Appl. No.: 14/750,645

(22) Filed: Jun. 25, 2015

(65) Prior Publication Data

US 2015/0289871 A1 Oct. 15, 2015

Related U.S. Application Data

(63) Continuation of application No. PCT/CN2013/090561, filed on Dec. 26, 2013.

(30) Foreign Application Priority Data

Dec. 28, 2012 (CN) .......................... 2012 1 0582075

(51) Int. Cl.
*A61B 17/10* (2006.01)
*A61B 17/04* (2006.01)
(Continued)

(52) U.S. Cl.
CPC .......... *A61B 17/068* (2013.01); *A61B 17/072* (2013.01); *A61B 2017/00539* (2013.01);
(Continued)

(58) Field of Classification Search
CPC ............ A61B 17/068; A61B 17/07207; A61B 2017/07271; A61B 2017/00539
(Continued)

(56) References Cited

U.S. PATENT DOCUMENTS 3,888,003 A * 6/1975 Brown ..................... B25B 7/126
140/106
4,331,277 A * 5/1982 Green ................ A61B 17/0684
227/130

(Continued)

FOREIGN PATENT DOCUMENTS

| CN | 101305928 A | 11/2008 |
| CN | 101534725 A | 9/2009 |

(Continued)

OTHER PUBLICATIONS

International Search Report, dated Mar. 27, 2014, for International Application No. PCT/CN2013/090561, 6 pages.

*Primary Examiner* — Robert Long
(74) *Attorney, Agent, or Firm* — Seed IP Law Group LLP

(57) ABSTRACT

A firing assembly for a surgical stapler includes a shell, a pressure chamber arranged in the shell to accommodates fluid, an ejector rod located below the shell to provide an actuated force and press the fluid in the pressure chamber, a number of piston holes communicating with the pressure chamber, a number of pistons received in the piston holes and a number of firing portions actuated by the pistons. The firing action of the stapler is gentle and the stapling effect for the anastomosed tissues is uniform.

16 Claims, 5 Drawing Sheets

(51) Int. Cl.
  *A61B 17/068* (2006.01)
  *A61B 17/072* (2006.01)
  *A61B 17/00* (2006.01)

(52) U.S. Cl.
  CPC ............ *A61B 2017/07242* (2013.01); *A61B 2017/07278* (2013.01)

(58) Field of Classification Search
  USPC ............ 227/175.1–182.1; 606/139, 142, 143
  See application file for complete search history.

(56) References Cited

U.S. PATENT DOCUMENTS

| | | | | |
|---|---|---|---|---|
| 4,586,502 | A * | 5/1986 | Bedi | A61B 17/04 606/144 |
| 4,621,639 | A | 11/1986 | Transue et al. | |
| 4,930,674 | A * | 6/1990 | Barak | A61B 17/072 227/179.1 |
| 4,951,861 | A * | 8/1990 | Schulze | A61B 17/072 227/130 |
| 4,962,877 | A * | 10/1990 | Hervas | A61B 17/115 227/179.1 |
| 5,005,754 | A * | 4/1991 | Van Overloop | A61B 17/072 227/178.1 |
| 5,163,598 | A * | 11/1992 | Peters | A61B 17/0686 227/124 |
| 5,197,649 | A * | 3/1993 | Bessler | A61B 17/1114 227/156 |
| 5,219,111 | A * | 6/1993 | Bilotti | A61B 17/072 227/175.1 |
| 5,411,508 | A * | 5/1995 | Bessler | A61B 17/1114 227/179.1 |
| 5,658,300 | A * | 8/1997 | Bito | A61B 17/1285 227/176.1 |
| 5,782,397 | A * | 7/1998 | Koukline | A61B 17/0686 227/119 |
| 5,833,695 | A * | 11/1998 | Yoon | A61B 17/072 227/176.1 |
| 5,862,972 | A * | 1/1999 | Green | A61B 17/0684 227/175.1 |
| 5,868,760 | A * | 2/1999 | McGuckin, Jr. | A61B 17/00234 227/179.1 |
| 6,387,113 | B1 * | 5/2002 | Hawkins | A61B 17/064 227/180.1 |
| 6,491,201 | B1 * | 12/2002 | Whitman | A61B 17/1114 227/180.1 |
| 7,077,856 | B2 * | 7/2006 | Whitman | A61B 5/6885 606/219 |
| 7,434,716 | B2 * | 10/2008 | Viola | A61B 17/07207 227/176.1 |
| 7,641,095 | B2 * | 1/2010 | Viola | A61B 17/07207 227/176.1 |
| 7,766,207 | B2 * | 8/2010 | Mather | A61B 17/072 227/175.1 |
| 7,934,631 | B2 * | 5/2011 | Balbierz | A61B 17/068 227/176.1 |
| 8,021,373 | B2 * | 9/2011 | Whitman | A61B 17/07207 606/139 |
| 9,016,541 | B2 * | 4/2015 | Viola | A61B 17/072 227/176.1 |
| 9,421,006 | B2 * | 8/2016 | Baker | A61B 17/00234 |
| 2003/0105478 | A1 * | 6/2003 | Whitman | A61B 17/07207 606/167 |
| 2004/0002726 | A1 * | 1/2004 | Nunez | A61B 17/02 606/192 |
| 2004/0097982 | A1 * | 5/2004 | Jugenheimer | A61B 17/122 606/151 |
| 2007/0106317 | A1 * | 5/2007 | Shelton, IV | A61B 17/07207 606/170 |
| 2008/0078804 | A1 | 4/2008 | Shelton et al. | |
| 2008/0110958 | A1 | 5/2008 | McKenna et al. | |
| 2009/0302092 | A1 * | 12/2009 | Kasvikis | A61B 17/072 227/180.1 |
| 2010/0170931 | A1 * | 7/2010 | Viola | A61B 17/128 227/175.1 |
| 2011/0248064 | A1 * | 10/2011 | Marczyk | A61B 17/07207 227/114 |
| 2011/0282381 | A1 * | 11/2011 | Cronin | A61B 10/0275 606/213 |
| 2012/0168487 | A1 * | 7/2012 | Holsten | A61B 17/00491 227/176.1 |
| 2012/0223122 | A1 * | 9/2012 | Roy | A61B 17/072 227/175.1 |
| 2012/0228358 | A1 * | 9/2012 | Zemlok | A61B 17/072 227/176.1 |
| 2015/0048141 | A1 * | 2/2015 | Felder | A61B 17/11 227/179.1 |
| 2017/0189026 | A1 * | 7/2017 | Felder | A61B 17/07207 |

FOREIGN PATENT DOCUMENTS

| | | |
|---|---|---|
| CN | 103142269 A | 6/2013 |
| CN | 203029297 U | 7/2013 |

\* cited by examiner

FIRING ASSEMBLY FOR SURGICAL STAPLER AND SURGICAL STAPLER

TECHNICAL FIELD

The present application relates to a technical field of medical apparatus and instruments, especially relates to a firing assembly for a surgical stapler and a surgical stapler with the firing assembly.

BACKGROUND

It has been nearly a century since the surgical stapler is used for alimentary tract anastomosis. Generally, the surgical staplers can be divided into many types, such as disposable surgical stapler, reusable surgical stapler, import surgical stapler or domestic surgical stapler. The surgical stapler is a device to replace a traditional manual suturing device in the medical field. With an improvement of manufacturing technology and a development of modern science and technology, the surgical stapler now in clinical use is high quality, easy to use, tight and snug fit, which especially has some advantages that fast suturing, easy operation and few side effects and complications, etc. Sometimes, using the surgical staple can also resect a tumor that used to be difficult or impossible to resect. So, the staples are highly favored by domestic and foreign clinical surgeons.

SUMMARY

Referring to FIG. 1, generally, the surgical stapler includes a body portion 10, a staple cartridge assembly 20, an anvil assembly 30 and a firing structure. The firing structure includes a firing handle/pushing button 41, a firing assembly 42 connected between the firing handle and the staple cartridge assembly 20. As the connection of the traditional firing assembly and the firing handle and the staple cartridge assembly is pure mechanical, in use, the firing force is lack of flexibility and with a hard feeling. Further, under a limitation of the structure of the surgical stapler, the deformation of each staple is almost equal to each other in once firing process. In fact, the thickness of the body tissue is not uniform. Especially, in a surgery that the anastomosis incision is longer, the thickness of the tissue is hard to estimate. Thus, if the deformation of the staples meets a need of hemostasis for a thick tissue, the need of hemostasis for a thin tissue will not be fully meted, and will lead to a haemorrhage of the tissue. While, if the deformation of the staples meets a need of hemostasis for a thin tissue, an anastomosis of a thick tissue will be too tight, and a blood-supply and recovery of the anastomosis site will also be effected. An embodiment facilitates avoiding these disadvantages of a traditional surgical stapler.

In an embodiment, a firing assembly for a surgical stapler includes:

A shell;

A pressure chamber, which is arranged in the shell and accommodates fluid;

An ejector rod, which is located below the shell to provide an actuated force and press the fluid in the pressure chamber;

A number of piston holes, which communicate with the pressure chamber;

A number of pistons, which are received in the piston holes; and

A number of firing portions, which are actuated by the pistons.

In an embodiment, a surgical stapler includes a body portion and a firing assembly, wherein the firing assembly includes:

A shell;

A pressure chamber, which is arranged in the shell and accommodates fluid;

An ejector rod, which is located below the shell to provide an actuated force and press the fluid in the pressure chamber;

A number of piston holes, which communicate with the pressure chamber;

A number of pistons, which are received in the piston holes; and

A number of firing portions, which are actuated by the pistons.

Comparing with the prior arts, the firing assembly for a surgical stapler of an embodiment has a firing action which is gentle, which may facilitate that the anastomosis of the staples is uniform and the postoperative effect is good.

ILLUSTRATED EMBODIMENTS

Figure 1:
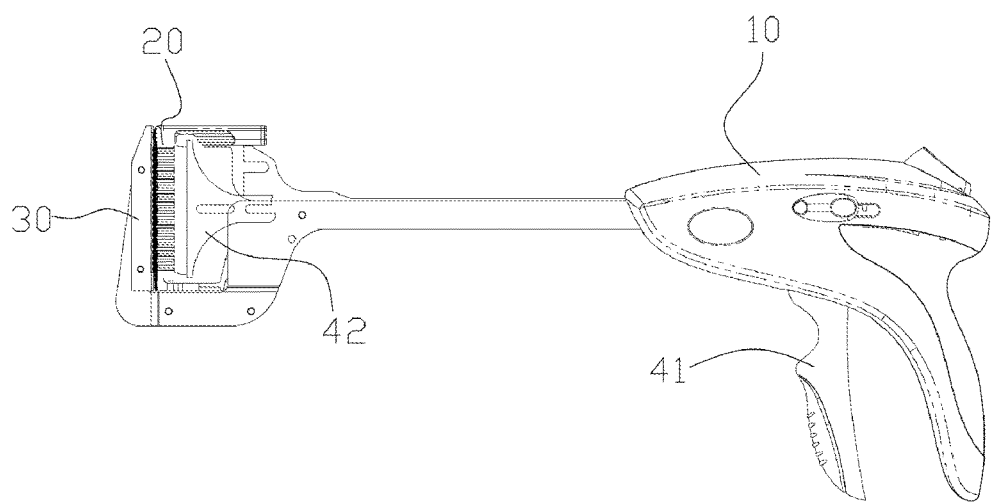
FIG. 1 is a partial perspective view of a surgical stapler for a prior art.
Figure 2:
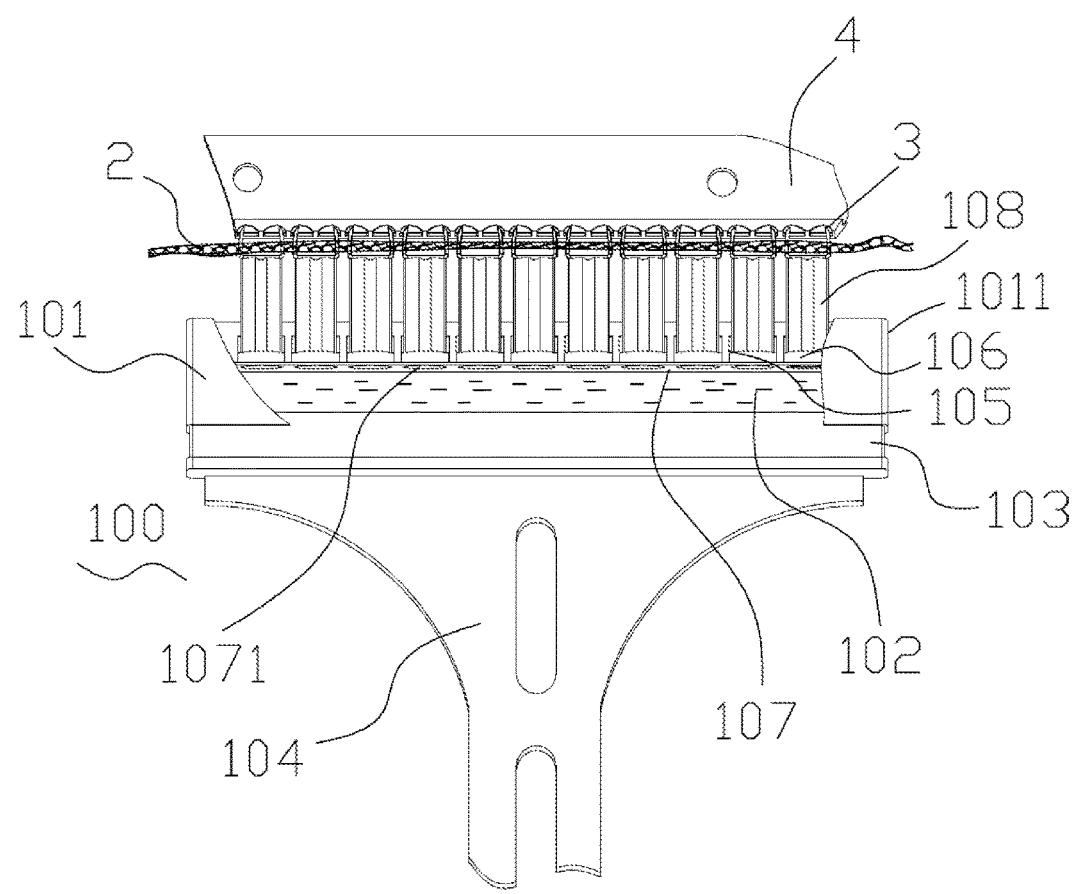
FIG. 2 a schematic structural view of a firing assembly for a surgical stapler in accordance with an illustrated embodiment of the present application, when it is at its initial status.
Figure 3:
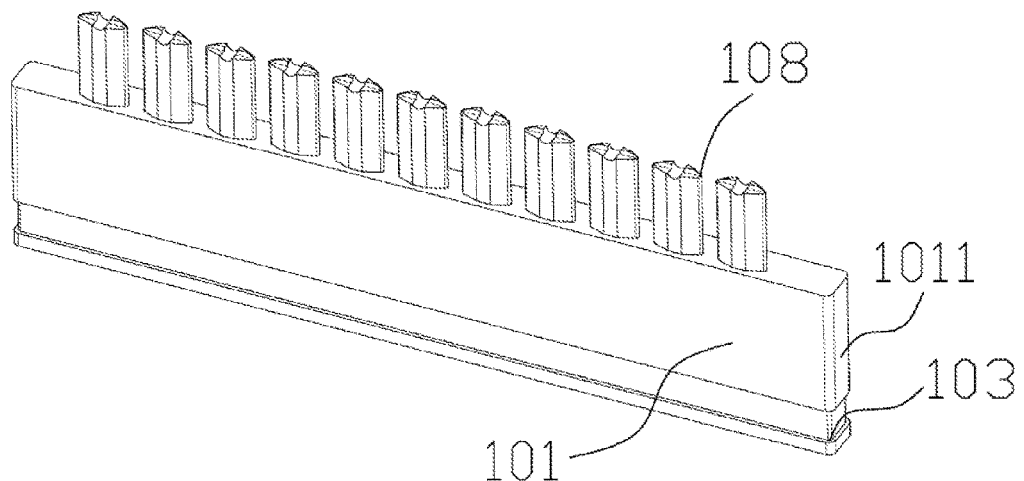
FIG. 3 is a partial perspective view of the firing assembly for the surgical stapler, the scaling factor for which is different from what for the FIG. 1.
Figure 4:
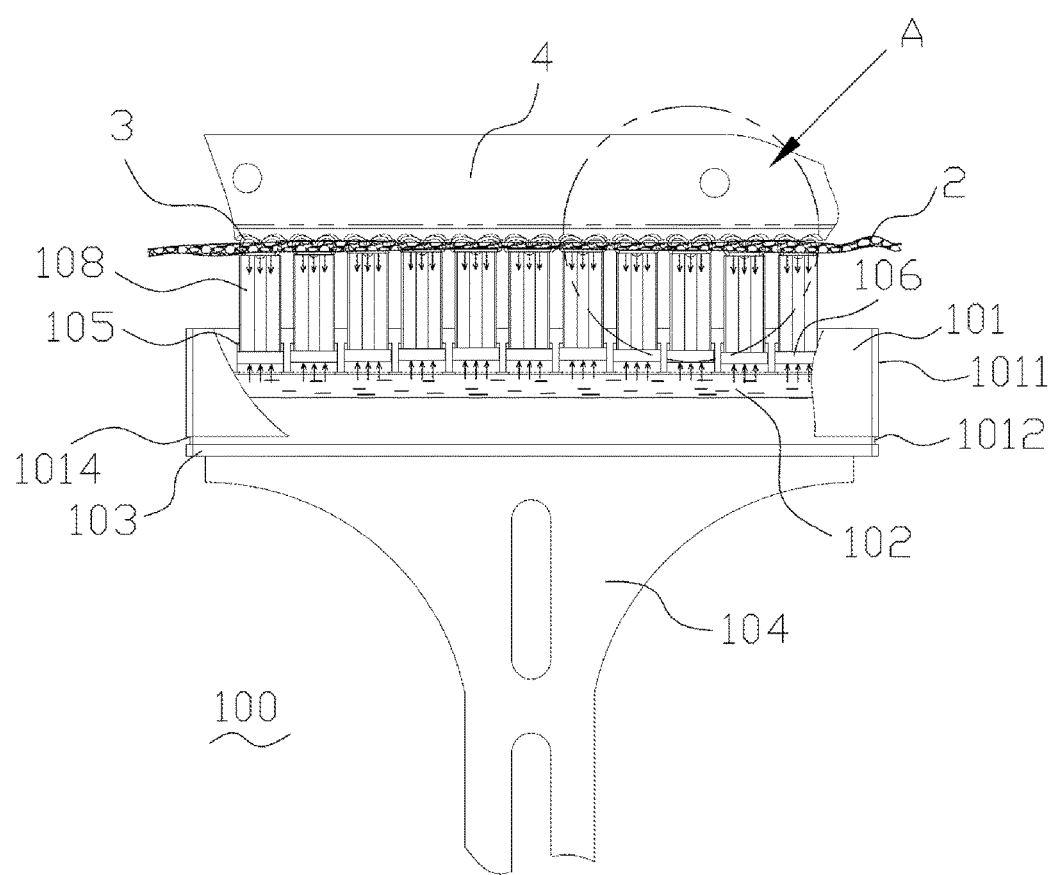
FIG. 4 a schematic structural view of the firing assembly for the surgical stapler when it is at its initial status, wherein the arrows show a force applied thereof.

Reference will now be made to the drawing figures to describe example embodiments in detail. It should be stated that, the embodiments should not be construed as limiting; all the function, methods or structure formed by the equivalent modification or the equivalent variation by an ordinary skilled person in the art, fall into the protection scope of the present application.

In the detailed description of the present embodiment, referring to the drawing figures and the brief description thereof will make an understanding of the embodiment easier. The main disclosure is generally directed to embodiments of firing assemblies and the other parts of the surgical stapler will not be described in detail.

Referring to FIGS. 2 to 5, the present application provides a firing assembly 100 for a surgical stapler. The firing assembly 100 has a shell 101 with a pair of guiding recesses 1012, 1014 defined in a pair of sidewalls 1011 thereof. The shell 101 has a pressure chamber 102 arranged therein to accommodate fluid. The fluid is, for example, liquid or gas. An assistor 103 is provided below the pressure chamber 102 and has a sealed connection with the pressure chamber 102. A pair of sidewalls of the assistor 103 are received in the guiding recesses 1012 and 1014 and moves therein. An ejector rod 104 is provided below the assistor 103 to push the assistor 103 moving upwardly and thereby compressing the fluid in the pressure chamber 102. Of course, easy to understand, the assistor 103 and the ejector rod 104 may be formed integrally in an embodiment.

The firing assembly 100 further has a plurality of piston holes 105 communicating with the pressure chamber 102 and a plurality of pistons 106 sealed in the piston holes 105. A spacer 107 is provided between the piston holes 105 and the pressure chamber 102, which is arranged at a bottom position of the piston holes 105. Corresponding to the position of the piston holes 105, the spacer 107 defines a plurality of through holes 1071 therethrough to ensure a communication of the pressure chamber 102 and the piston holes 105. Of course, the arrangement of the spacer 107 and the through holes 1071 can be modified to another means, such as a number of restriction members are provided in the piston holes 105. Of course, it is understand that, the restriction members are open in some way, and consequently a pressure of the fluid in the pressure chamber 102 is transmitted to a bottom surface of the pistons 106 and a force is applied on the pistons 106.

A plurality of firing portions 108 are correspondingly provided above each pistons 106, each of which is movable in an axial direction of the pistons 106 independently. Of course, some of the firing portions 108 in independent or group settings are set with the same effect. To arrange the firing portions 108 in independent or group settings depends on the specific situation.

When the firing assembly 100 in accordance with at embodiment is at its initial status, the pressure of the fluid in the pressure chamber 102 is equal to that of the outside, and consequently the pistons 106 are in a stationary status. In the firing process, the ejector rod 104 is pushed to press the fluid in the pressure chamber 102 via the assistor 103, and consequently the pressure in the pressure chamber 102 increases and generates an upward pushing force (as shown by the arrows in FIG. 4). As the pressure chamber 102 communicates with the piston holes 105 via the through holes 1071, the increased pressure in the piston holes 105 will push the pistons 106 moving upwardly, and consequently drives the firing portions 108 moves upwardly too. Now, the staples 3 arranged on the firing portions 108 will be ejected out and staple the anastomosed tissue 2. When the firing portions 108 move upwardly, the feet of the staples 3 is bent down to form a shape of "B" as they abut against the anvil 4.

At a first stage of the deformation of the firing portions 108, the formed heights of the staples 3 are equal to each other. While, with the further bending of the feet of the staples 3, the anastomosed tissue 2 stapled by the staples 3 will also generate a downward reacting force after which is pressed by an acting force (as shown by the arrows in FIG. 4). Now, for a part of the firing portions 108 located at an area where the anastomosed tissue 2 is thick, the reacting force applied thereto from the anastomosed tissue 2 is larger, which will first get a balance with the acting force applied to this part of the firing portions 108 from the pistons 106 since the pistons 106 are forced by the fluid. With the force balance, the deformation of staples 3 arranged at an area where the anastomosed tissue 2 is thick will be stopped. For another part of the firing portions 108 located at an area where the anastomosed tissue 2 is thin, another reacting force applied thereto from the anastomosed tissue 2 is smaller, which is still not smaller than the acting force applied to this part of the firing portions 108 from the pistons 106 since the pistons 106 are forced by the fluid. So, the staples 3 located at the area where the anastomosed tissue 2 is thin will be deformed further and the anastomosed tissue 2 will be stapled tightly, until the reacting force applying to the firing portions 108 form the anastomosed tissue 2 reaches a balance with the force applied to the firing portions 108 from the fluid.

Figure 5:
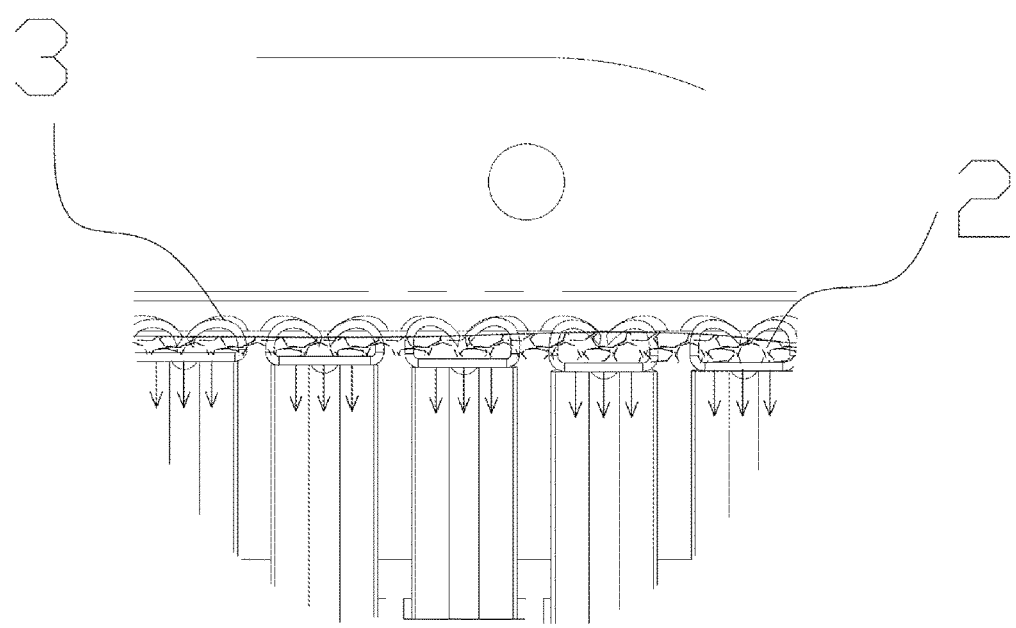
FIG. 5 is an enlarged view of structures in the circle A as shown in FIG. 4, to show the different formed heights of the staples.

According to the basic properties that the fluid can transfer pressure, as long as the pistons 106 are with the same area, the acting force applied to the firing portions 108 from the pistons 106 will be equal to each other, and consequently a stapling effect for all the anastomosed tissues 2 will be same, even that the formed heights of the staples 3 are different from each other (referring to FIG. 5).

The firing assembly in accordance with various embodiments may be used for various types of surgical staplers, including linear cutter, circular stapler, curved cutter stapler. Any type surgical staplers with the firing assembly in accordance with the present disclosure may be employed. In an embodiment, the fluid pressure is applied to adjust the formed heights of the staples, resulting that the firing action is gentle and accords with human body engineering principle. In addition, the formed heights of the staples vary due to a thickness of anastomosed tissues, which facilitates that the ultimately stapling effect for the anastomosed tissues is uniform.

For the person skilled in the art, the present disclosure is not limited to details of the exemplary embodiments; and changes may be made in detail within the spirit of and the principles of present disclosure to implement. Therefore, for every point, the above description should be construed merely as exemplifications of example embodiments, not as limiting. The drawing reference numerals should not be construed as limiting.

In addition, it should be understood, although the specification is described in accordance with the implementation of the embodiment, but not every embodiment contains only an independent technical proposal. This kind of description for the specification is just for the sake of clarity. The person skilled in the art should consider the specification as a whole. The technical proposals of the every embodiment can also be combined in a proper way to form another embodiment that the person skilled in the art can understand.

What is claimed is:

1. A firing assembly for a surgical stapler, comprising:
   a shell;
   a pressure chamber, which is arranged in the shell and accommodates fluid;
   an ejector rod, which is located below the shell to provide an actuated force and press the fluid in the pressure chamber;
   a plurality of piston holes, which communicate with the pressure chamber;
   a plurality of pistons, which are received in the piston holes; and
   a plurality of firing portions for firing surgical staples, actuated by the pistons, wherein each of the firing portions is arranged over respective pistons and wherein each of the firing portions is independent from each other.

2. The firing assembly as claimed in claim 1 wherein a restriction member is provided between the piston holes and the pressure chamber to limit a movement of the pistons in the piston holes.

3. The firing assembly as claimed in claim 2 wherein the restriction member is a spacer arranged at a bottom position of the piston holes, and wherein the spacer defines a plurality of through holes corresponding to the piston holes.

4. The firing assembly as claimed in claim 1 wherein the fluid in the pressure chamber is liquid.

5. The firing assembly as claimed in claim 1 wherein the fluid in the pressure chamber is gas.

6. The firing assembly as claimed in claim 1 wherein a pair of guiding recesses are defined in sidewalls of the shell to receive an assistor therein, and wherein the assistor presses the fluid in the pressure chamber via the movement of ejector rod.

7. The firing assembly as claimed in claim 1 wherein the shell defines a pair of guiding recesses in sidewalls thereof to receive an assistor at a front end of the ejector rod therein, and wherein the assistor presses the fluid in the pressure chamber.

8. A surgical stapler, which comprises a body portion and a firing assembly, wherein the firing assembly comprises:
   a shell;
   a pressure chamber, which is arranged in the shell and accommodates fluid;
   an ejector rod, which is located below the shell to provide an actuated force and press the fluid in the pressure chamber;
   a plurality of piston holes, which communicate with the pressure chamber;
   a plurality of pistons, which are received in the piston holes; and
   a plurality of firing portions for firing surgical staples, actuated by the pistons, wherein each of the firing portions is arranged over respective pistons and wherein each of the firing portions is independent from each other.

9. The surgical stapler as claimed in claim 8 wherein a restriction member is provided between the piston holes and the pressure chamber to limit a movement of the pistons in the piston holes.

10. The surgical stapler as claimed in claim 9 wherein the restriction member is a spacer arranged at a bottom position of the piston holes, and wherein the spacer defines a plurality of through holes corresponding to the piston holes.

11. The surgical stapler as claimed in claim 8 wherein the fluid in the pressure chamber is liquid.

12. The surgical stapler as claimed in claim 8 wherein the fluid in the pressure chamber is gas.

13. The surgical stapler as claimed in claim 8 wherein a pair of guiding recess are defined in sidewalls of the shell to receive an assistor therein, and wherein the assistor presses the fluid in the pressure chamber via the movement of ejector rod.

14. The surgical stapler as claimed in claim 8 wherein the shell defines a pair guiding recesses in sidewalls thereof to receive an assistor at a front end of the ejector rod therein, and wherein the assistor presses the fluid in the pressure chamber.

15. The surgical stapler as claimed in claim 8 wherein a plurality of restriction members are provided in the piston holes and wherein the restriction members are open to result that the piston holes communicate with the pressure chamber.

16. The surgical stapler as claimed in claim 13 wherein the assistor and the ejector rod are formed integrally.

* * * * *